United States Patent
Akahane et al.

(10) Patent No.: US 8,545,024 B2
(45) Date of Patent: Oct. 1, 2013

(54) OPHTHALMIC APPARATUS

(75) Inventors: Yoko Akahane, Gamagori (JP); Tatefumi Oda, Nukata-gun (JP)

(73) Assignee: Nidek Co., Ltd., Gamagori-Shi (JP)

(*) Notice: Subject to any disclaimer, the term of this patent is extended or adjusted under 35 U.S.C. 154(b) by 79 days.

(21) Appl. No.: 13/029,543

(22) Filed: Feb. 17, 2011

(65) Prior Publication Data

US 2011/0211160 A1   Sep. 1, 2011

(30) Foreign Application Priority Data

Feb. 26, 2010   (JP) .................................. 2010-042512

(51) Int. Cl.
  *A61B 3/00*   (2006.01)
  *A61B 3/14*   (2006.01)
(52) U.S. Cl.
  USPC .......................................... 351/245; 351/206
(58) Field of Classification Search
  USPC .................................................. 351/206, 245
  See application file for complete search history.

(56) References Cited

U.S. PATENT DOCUMENTS

2008/0297725 A1   12/2008   Mimura

FOREIGN PATENT DOCUMENTS

| JP | A 2003-235810 | 8/2003 |
| JP | A 2006-026096 | 2/2006 |
| JP | A 2006-055439 | 3/2006 |

*Primary Examiner* — Jack Dinh
(74) *Attorney, Agent, or Firm* — Oliff & Berridge, PLC

(57) ABSTRACT

An ophthalmic apparatus comprises: a main unit including a photographing device for photographing an examinee's eye; a monitor provided in the main unit, the monitor including a displaying device for displaying an image of the eye photographed by the photographing device and a setting device for setting a predetermined function; a rotation mechanism for rotating the monitor from an almost vertical position to an almost horizontal position with respect to the main unit; a first lock mechanism for locking the monitor at each predetermined tilt angle, the first lock mechanism being arranged to allow upward rotation of the monitor but restrict downward rotation of the monitor in the course of rotating the monitor from the almost vertical position to the almost horizontal position; and a first unlock mechanism arranged to release the restriction of the downward rotation of the monitor by the first lock mechanism based on further upward rotation of the monitor after the monitor is locked in a first maximum tilt lock position by the first lock mechanism.

6 Claims, 9 Drawing Sheets

OPHTHALMIC APPARATUS

CROSS-REFERENCE TO RELATED APPLICATIONS

This application is based upon and claims the benefit of priority from the prior Japanese Patent Application No. 2010-042512, filed on Feb. 26, 2010, the entire contents of which are incorporated herein by reference.

TECHNICAL FIELD

The present invention relates to an ophthalmic apparatus for examining an eye of an examinee.

BACKGROUND ART

An ophthalmic apparatus includes an examination optical system for examining (measuring, observing, or photographing) an eye of an examinee and a monitor fixed in front of a main unit of the apparatus to display an image of the examinee's eye (hereinafter, referred to as a photographed image) captured by a camera (a photographing means). An examiner performs alignment between the examination optical system and the examinee's eye by operation of a joystick (an operation member) or the like while observing the photographed image displayed on the monitor. Further, there is known an apparatus provided with a monitor having a touch panel function so that various functions are set on the touch panel (JP 2003-235810 A).

In a conventional ophthalmic apparatus, a monitor is fixed in an almost vertical state (including a little tilted state) with respect to an installation plane (an examiner's side) of the main unit of the apparatus in order to make the photographed image displayed on the monitor easily viewable to an examiner who is sitting. Accordingly, if the examinee opens his/her eyelids sufficiently wide, the examiner in a sitting position can perform an examination while observing the photographed image displayed on the monitor. On the other hand, if the examinee does not open his/her eyelids wide, the examiner has to perform the examination by extending his/her arm to lift up the examinee's eyelid with examiner's fingers while observing the front monitor of the apparatus. In this case, the examiner in the sitting position is forced to take an unnatural posture and could not easily operate the apparatus for ophthalmic examinations.

Therefore, the monitor is rotatably attached to the main unit of the apparatus. The monitor is configured to be tilted from an almost vertical position with respect to an installation plane of the apparatus main unit to an almost horizontal position in which a display screen of the monitor is turned upward. This makes it possible to facilitate observation of the photographed image displayed on the monitor irrespective of the differences in examiner's position, sitting or standing. For instance, the monitor is rotatably attached to the apparatus main unit via a free stop hinge. Thus, when a predetermined force or more is applied on the monitor, the monitor is made tilt and swing. Under no force, the monitor is kept at a predetermined tilt angle by a frictional force of a hinge (JP 2006-26096 A).

SUMMARY OF INVENTION

Technical Problem

Meanwhile, for further facilitating operator's operation, the monitor with a rotation mechanism is demanded to include a touch panel. However, the monitor configured to be tilted through the free stop hinge is liable to oscillate by a press on the touch panel during operation or is forced to change the tilt angle by a press on the touch panel. When the monitor is oscillated by operation of the touch panel, the examiner's finger may touch the touch panel more than one time and thus could not correctly perform an input operation. Furthermore, for facilitating input from the touch panel, the monitor is preferred to be as wide and easy to view as possible. However, in the configuration having the problem with monitor oscillation as in the conventional technique, increasing the size of the monitor leads to greater oscillation of the monitor.

The present invention has been made to solve the above problems and has a purpose to provide an ophthalmic apparatus capable of changing a tilt angle at which a monitor of an apparatus main unit is easy to view to an examiner irrespective of his/her position and capable of appropriate handling the monitor even when the monitor includes a touch panel or the like.

Solution to Problem

To achieve the above purpose, one aspect of the invention provides an ophthalmic apparatus comprising: a main unit including a photographing device for photographing an examinee's eye; a monitor provided in the main unit, the monitor including a displaying device for displaying an image of the eye photographed by the photographing device and a setting device for setting a predetermined function; a rotation mechanism for rotating the monitor from an almost vertical position to an almost horizontal position with respect to the main unit; a first lock mechanism for locking the monitor at each predetermined tilt angle, the first lock mechanism being arranged to allow upward rotation of the monitor but restrict downward rotation of the monitor in the course of rotating the monitor from the almost vertical position to the almost horizontal position; and a first unlock mechanism arranged to release the restriction of the downward rotation of the monitor by the first lock mechanism based on further upward rotation of the monitor after the monitor is locked in a first maximum tilt lock position by the first lock mechanism.

DESCRIPTION OF EMBODIMENTS

Figure 1:
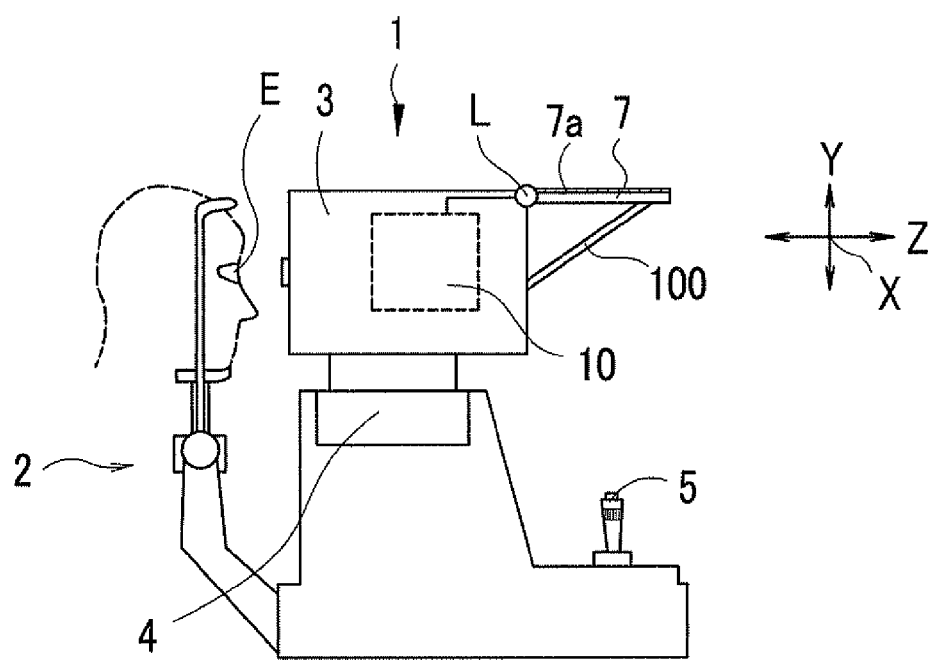
FIG. 1 is an external schematic explanatory view of an ophthalmic apparatus.

A detailed description of a preferred embodiment of the present invention will now be given referring to the accompanying drawings. FIG. 1 is an external schematic explanatory view of an ophthalmic apparatus. FIGS. 2A to 2D are explanatory views to show a relationship between an apparatus main unit and a monitor. In the present embodiment, an ophthalmic apparatus is exemplified as an eye refractive power measuring apparatus for measuring eye refractive power of an eye of the examinee. However, not limited thereto, the present invention is applicable to an ophthalmic apparatus having a monitor for displaying the eye in order to examine (measure, observe, photograph, etc.) the eye.

In a main unit 1 on an examinee's side, a head fixing unit 2 is fixedly provided to fix the head of the examinee. An examination unit 3 housing therein a measurement part 10 is mounted in an upper section of the main unit 1. The examination unit 3 is moved in three dimensional directions (X, Y, and Z directions) with respect to the examinee's eye E by a drive mechanism 4 (a movement unit) placed in the main unit 1. The measurement part 10 includes a known photographing and measuring optical system of photographing the eye E and determine refractive power thereof, a controller, and others. The drive mechanism 4 includes, for each movement direction, a known movement mechanism consisting of a motor and a slide mechanism.

A monitor 7 is placed on an examiner's side of the main unit 1. The monitor 7 includes a liquid crystal monitor for displaying a photographed image and information to the examiner and a touch panel (a pointing device) 7a placed on the liquid crystal monitor. The examiner touches the touch panel 7a with his/her finger, a touch pen, or the like to input a signal for setting various measurement conditions and others. It is to be noted that such monitor 7 is preferably configured to have e.g., a 8 to 12-inch size to make input operations on the touch panel 7a easier to the examiner. The monitor 7 is mounted in a holder or frame made of a steel plate or a thick resin material to keep a surface flat (not shown).

A known rotation mechanism L such as a hinge is attached between an upper end of the monitor 7 and a front surface (on the examiner's side) of the main unit 1. Thus, the monitor 7 is rotated through the rotation mechanism L from an almost vertical position (a reference position) to an almost horizontal position in which a screen is turned upward. The monitor 7 is electrically connected to the measurement part 10 placed in the examination unit 3. Accordingly, a photographed image and a measurement result of the eye E obtained by the measurement part 10 are displayed on the liquid crystal monitor, and a command signal from the touch panel 7a is transmitted to the measurement part 10.

Further, a rotation restricting member 100 is provided between the monitor 7 and the main unit 1. When the monitor 7 reaches a predetermined tilt angle, the rotation restricting member 100 locks the monitor 7 against downward pressure applied to the monitor 7. It is to be noted that the rotation restricting member 100 in this embodiment consists of two different type components (a ratchet 110 and a stay 250, see FIGS. 3A and 4A). The monitor 7 is locked (stopped) at each different tilt position by the rotation restricting member 110 (the ratchet 110 and the stay 250).

Figure 2A:
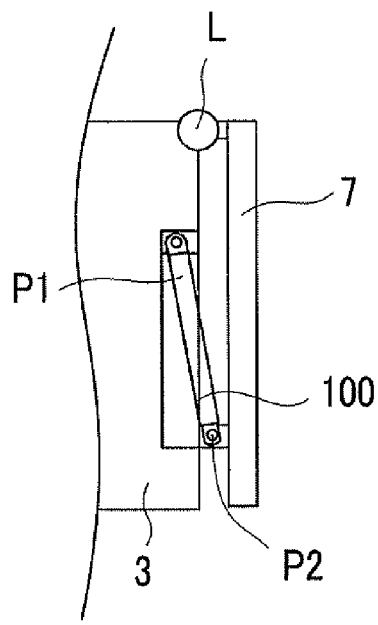
FIGS. 2A to 2D are explanatory views to show a relationship between an apparatus main unit and a monitor.
Figure 2B:
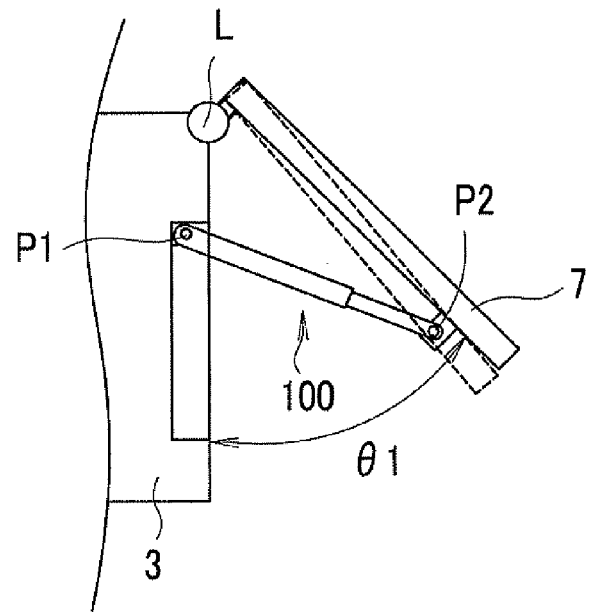
Figure 2C:
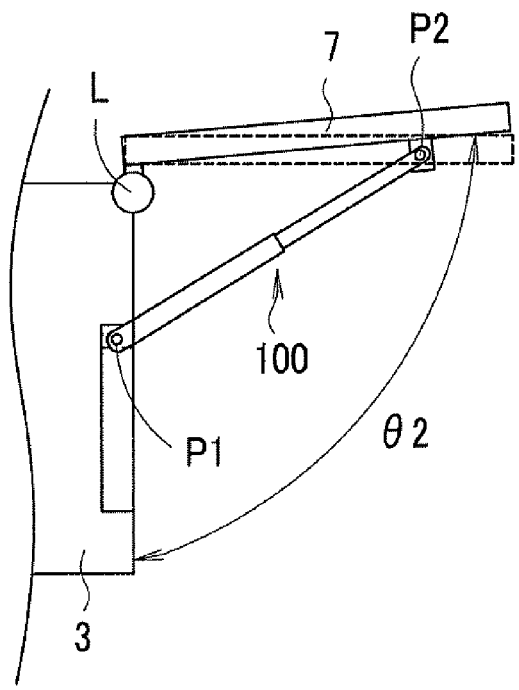
Figure 2D:
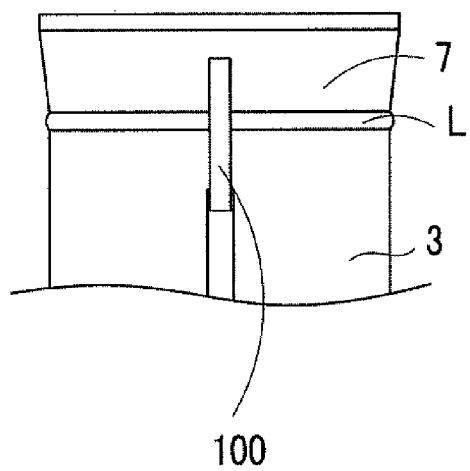

The ratchet 110 and the stay 250 of the rotation restricting member 100 are arranged in a bundle state with one end of the bundle is attached to near the center of a back side of the monitor 7 (fee FIG. 2D). Thus, the rotation restricting member 100 can extend and contract in synchronization with rotation of the monitor 7 about a connecting position of the main unit 1 and the monitor 7 (the details will be mentioned later).

The attachment position of the rotation restricting member 100 is not limited to the above. For instance, the rotation restricting member 100 may be attached to each side, right and left, of the monitor 7. As another alternative, if the ratchet 110 and the stay 250 are each configured to have a strength enough to hold the monitor 7, the ratchet 110 and the stay 250 may be attached separately to the center or the right and left sides of the monitor 7.

The monitor 7 in the present embodiment is arranged to rotate from an almost vertical angle (an initial position) to an almost horizontal angle with respect to an installation plane of the main unit 1 by the rotation restricting member 100. To be concrete, assuming that the vertical position to the installation plane of the main unit 1 is a reference position (an angle 0°), the monitor 7 is rotated in a range of 0° to 93°. When the monitor 7 is rotated up to a maximum tilt angle θ2 (herein, 93°), the stay 250 mentioned later locks the monitor 7 in the almost horizontal position. On the other hand, when the monitor 7 is rotated to a smaller tilt angle than the maximum tilt angle θ2 (a maximum tilt angle from the almost vertical position), the ratchet 110 locks the monitor 7 stepwise (e.g., at 30°, 45°, 60°, 75°, and 85°) according to the tilt angle. The above lock (stop) positions of the monitor 7 by the stay 250 and the ratchet 110 are determined to arbitrary angles in design. Herein, the maximum tilt lock position by the ratchet 110 is referred to as a "first maximum tilt lock position" and the lock position by the stay 250 is referred to as a "second tilt lock position".

Since the member for locking the monitor 7 at the maximum tilt angle (herein, the almost horizontal position) and the member for locking the monitor 7 stepwise in the rotatable range (excepting the maximum tilt angle) are combined as above, the monitor 7 can be surely locked once when the monitor 7 is tilted in the rotatable range. When the examiner is about to lock the monitor 7 at the maximum tilt angle, especially, he/she is allowed to easily lock the monitor 7 without concern for unintended unlocking of the monitor 7 resulting from rotation. Also, the monitor 7 can be locked at the maximum tilt angle without needing a great deal of time.

In relation to an ophthalmic apparatus, in many cases, an examiner views a monitor in a sitting position or a standing position while helping an examinee's eye open by lifting up his/her eyelid. Therefore, the rotation restricting member 100 is preferred to lock the monitor 7 at least in the almost horizontal position. When the monitor 7 is in the almost horizontal position, it is preferable that a display surface of the monitor 7 is located on the same level as or slightly higher than the upper surface of the apparatus main unit.

In the present embodiment, after the monitor 7 is stopped once at the maximum tilt angle (the almost horizontal position in this embodiment) and locked therein, when the monitor 7 is slightly rotated upward again, the monitor 7 is easily unlocked. Thus, the examiner can easily return the monitor 7 to the initial position (the almost vertical position).

A structure of the rotation restricting member 100 will be explained below. As mentioned above, the rotation restricting member 100 including the ratchet 110 and the stay 250 is placed between the monitor 7 and the main unit 1 so that the rotation restricting member 100 is moved in synchronization with the monitor 7. The ratchet 110 includes a lock mechanism for allowing upward rotation but restricting downward rotation of the monitor 7 at each predetermined tilt angle (including the first maximum tilt lock position). On the other hand, the stay 250 includes a lock mechanism for allowing upward rotation but restricting downward rotation of the monitor 7 in the second tilt lock position having a tilt angle larger than that of the first maximum tilt lock position of the ratchet 110. Further, those ratchet 110 and stay 250 include unlock mechanisms for releasing restriction by each lock mechanism when the monitor 7 is rotated to a larger tilt angle than respective maximum tilt lock positions of the ratchet 110 (i.e., the first maximum tilt lock position) and the stay 250 (i.e., the second tilt lock position).

Figure 3A:
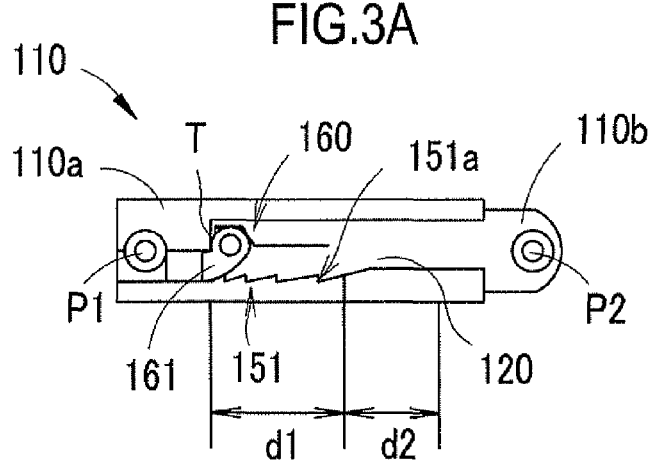
FIGS. 3A to 3D are explanatory views to show a structure of a ratchet of a rotation restricting member.
Figure 3B:
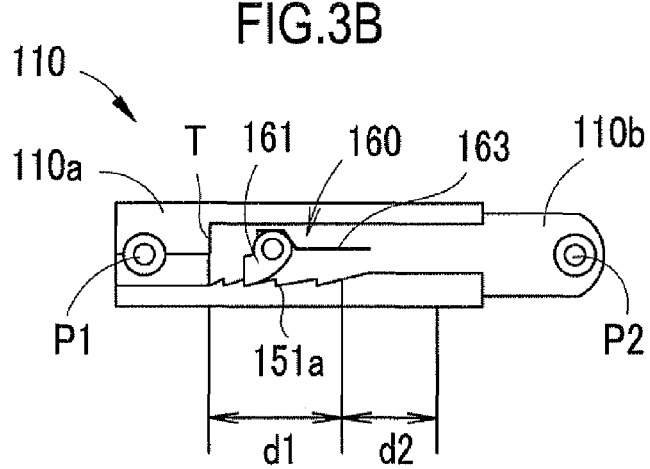
Figure 3C:
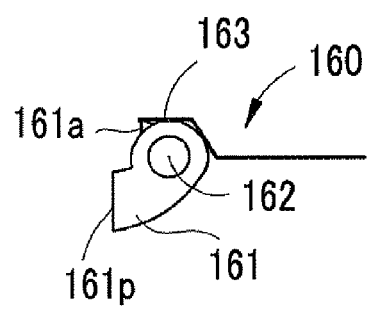
Figure 3D:
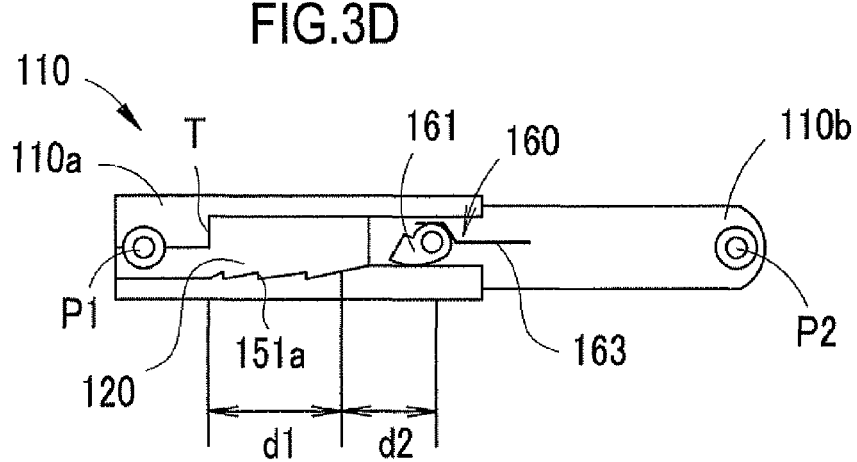

FIGS. 3A to 3D are schematic explanatory views to show the structure of the ratchet 110. Specifically, FIG. 3A shows the ratchet 110 in an initial position (a tilt angle θ=0°), FIG. 3B shows the ratchet 110 in a state when the monitor 7 has been rotated to a tilt angle θ1 shown in FIG. 2B, FIG. 3C shows an enlarged view of a pawl locking mechanism 160 (mentioned later), and FIG. 3D shows the ratchet 110 in another state when the monitor 7 has been rotated up to the maximum tilt angle θ2 shown in FIG. 2C.

Figure 4A:
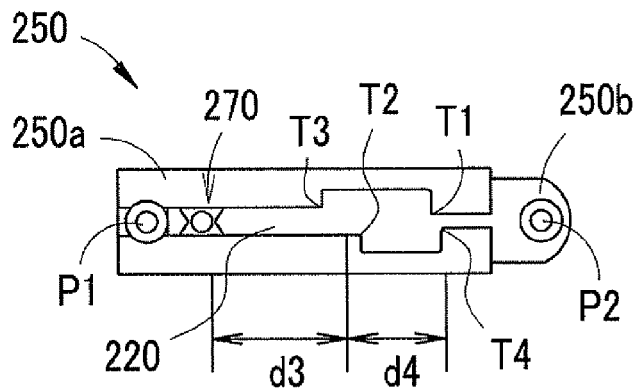
FIGS. 4A to 4D are explanatory view to show a structure of a stay of the rotation restricting member.
Figure 4B:
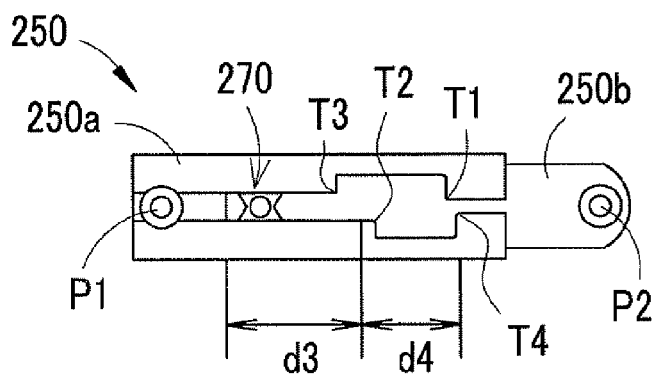
Figure 4C:
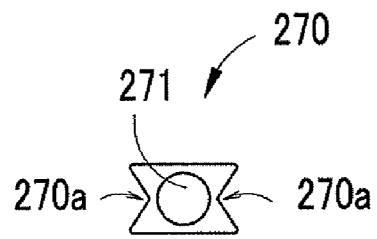
Figure 4D:
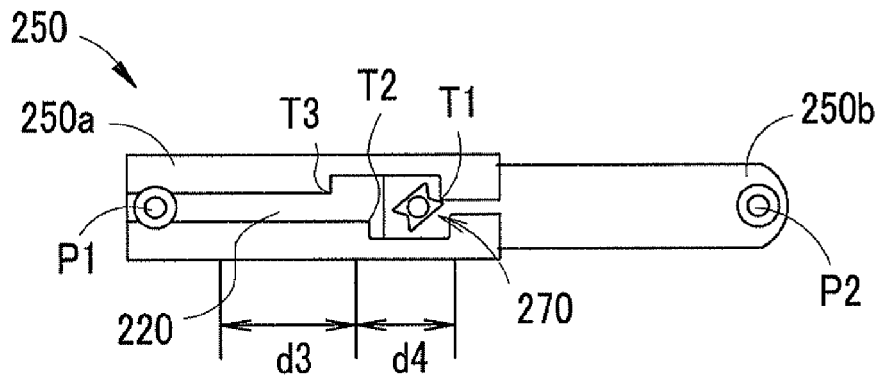

FIGS. 4A to 4D are schematic explanatory views of the stay 250. Specifically, FIG. 4 shows the stay 250 in an initial position (a tilt angle θ=0°), FIG. 4B shows the stay 250 in a state when the monitor 7 has been rotated to the tilt angle θ1, FIG. 4C is an enlarged view of a cam 270 (mentioned later) which is a rotation member, and FIG. 4D shows the stay 250 in another state when the monitor 7 has been rotated up to the maximum tilt angle θ2.

The ratchet 110 shown in FIGS. 3A to 3D consists of a fixed arm 110a and a movable arm 110b in combination. The fixed arm 110a is formed in a hollow flat plate-like shape. The movable arm 110b is formed in a flat plate-like shape having a size fittable in a hollow through hole (an insertion hole) of the fixed arm 110a. Further, the movable arm 110h is placed slidably in the through hole in the fixed arm 110a.

One end of the fixed arm 110a is provided with a fastening fitting P1 rotatable with respect to the fixed arm 110a. The fixed arm 110a is fixed to the main unit 1 through the fastening fitting P1. One end of the movable arm 110b is provided with a fastening fitting P2 rotatable with respect to the movable arm 110b. The movable arm 110h is fixed to the monitor 7 through the fastening fitting P2 (see FIG. 2). On the other hand, the other ends of the fixed arm 110a and the movable arm 110b are open ends so that the movable arm 110h slides inside the fixed arm 110a by rotation of the monitor 7. Thus, the ratchet 110 is held to extend and contract in its longitudinal direction.

The movable arm 110h is provided with the pawl locking mechanism 160. In FIG. 3C, the pawl locking mechanism 160 consists of a pin 162 fixed to the movable arm 110b, a pawl 161 integrally fitted on the pin 162 and rotatably attached to the movable arm 110b, and a leaf spring 163 which is an elastic member to apply pressure to the pawl 161 in one direction. A leading end 161p of the pawl 161 is designed to have such a size and shape as to engage with a serrate engagement portion 151 (mentioned later) formed in the fixed arm 110a. The pawl 161 is formed with a protrusion 161a. When this protrusion 161a is placed and pressed in contact with the leaf spring 163, the rotation angle of the pawl 161 is kept at a predetermined angle.

The fixed arm 110a is formed with the serrate engagement portion 151 in a predetermined range d1 in a passage 120 extending in a longitudinal direction. The engagement portion 151 engages with the pawl locking mechanism 160 of the movable arm 110b. Herein, the range d1 corresponds to a range in which the movable arm 110b is allowed to slide when the tilt angle of the monitor 7 is in a predetermined range (e.g., from 0° to 85° inclusive). The engagement portion 151 is formed with teeth (a lock stopper) 151a in positions corresponding to the tilt angles at each of which the monitor 7 is locked (the number of teeth is simplified for the sake of convenience in the figure). Each tooth 151a has such a shape as to allow forward movement of the pawl 161 in a direction to rotate the monitor 7 toward a horizontal position (in a direction to pull the movable arm 110b outward) and engage with the leading end 161a of the pawl 161 by movement of the pawl locking mechanism 160 in association with rotation of the monitor 7 in a direction to return to the initial position (a vertical position). The shape (slope) of the engagement portion 151 has a directional property that each tooth 151a has a gentle slope in a direction to pull the movable arm 110b to allow the pawl 161 to go across the teeth 151a but a steep slope in a direction to push the movable arm 110b back into the fixed arm 110a so that the pawl 161 engages with one tooth 151a without being allowed to go over the tooth 151a. Such ratchet mechanism allows rotation of the monitor 7 in one direction (upward) and locks the monitor 7 at each predetermined tilt angle in the opposite direction (downward).

A range d2 of the passage 120 beyond the range d1 of the fixed arm 110a formed with the engagement portion 151 in a forward movement direction of the movable arm 110b has a sloped surface for guiding rotation of the pawl 161 and positioning the leading end 161p to a rotation angle off the teeth 151a. When the movable arm 110b is pulled outward and then the pawl 161 goes in the passage range d2, the pawl 161 is rotated along the sloped surface formed in the range d2 until the leading end 161p reaches a position off the teeth 151a and then the protrusion 161a is fixed by the leaf spring 163. With such configuration, the rotation direction of the pawl 161 is fixed in a position where the leading end 161p does not engage with the engagement portion 151 and accordingly the movable arm 110b is allowed to return to the initial position (see FIG. 3D). The fixed arm 110a is formed, on the fastening fitting P1 side, with a contact portion T. When the leading end 161p of the pawl 161 comes into contact with the contact portion T, the pawl 161 is released from a fixed state by the leaf spring 163 of the pawl locking mechanism 160 to return to a position allowing the ratchet 110 to lock the monitor 7 again.

The stay 250 in FIGS. 4A to 4D consists of a combination of a fixed arm 250a formed in a hollow flat plate-like shape and a movable arm 250b formed in a flat plate-like shape having a size fittable in a hollow through hole (an insertion hole) of the fixed arm 250a. The fixed arm 250a and the movable arm 250b are provided with fastening fittings P1 and P2 respectively, each having the same function as the fastening fittings provided in the aforementioned ratchet 110. As with the ratchet 110, the stay 250 is connected to the main unit 1 and the monitor 7 through the fastening fittings P1 and P2 respectively. When the movable arm 250b slides inside the fixed arm 250a in synchronization with the rotation of the monitor 7, the stay 250 extends and contracts in its longitudinal direction.

The movable arm 250b is attached with a cam 270 pivotable about a pin 271. In the present embodiment, the cam 270 is of a rectangular shape with two constricted portions 270a recessed in a V-shape in each opposite short side (see FIG. 4C). This cam 270 and a passage 220 formed in the fixed arm 250a serve to lock and unlock the monitor 7 in a position beyond a lock position by the ratchet 110. The details thereof will be mentioned later.

In one side surface of the fixed arm 250a, the passage 220 engageable with the cam 270 of the movable arm 250b is formed to extend in the longitudinal direction. The width of the passage 220 in a range d3 of the passage 120 corresponding to the range d1 of the ratchet 110 formed with the engagement portion 151 is determined to be almost equal to the width of the short sides of the cam 270. On the other hand, a range d4 of the passage 220 of the fixed arm 250a corresponding to the passage range d2 of the ratchet 110 is designed to have a wider width allowing free rotation of the cam 270. In the passage range d4, further, contact portions T1 and T2 are formed to be engageable with the cam 270 to determine the rotation angle of the cam 270. This configuration provides a flap stay capable of making the cam 270 engage with the contact portion T1 or T2 in association with sliding-in and sliding-out motions of the movable arm 250b to lock and unlock sliding of the movable arm 250b.

The formation positions of the contact portions T1 and T2 will be explained below. The contact portion T1 is formed in a lower position than an upper end (a reference sign is not given thereto) in the range d3 of the passage 220 so that either one of the constricted portions 270a of the cam 270 moved from the range d3 to the range d4 comes into contact with the contact portion T1. On the other hand, the contact portion T2 is formed in a position closer to the contact portion T1 than an upper angular portion T3 in the range d3 of the passage 220 is in the longitudinal direction so that the opposite constricted portion 270a comes into contact with the contact portion T2 when the cam 270 having contacted with the contact portion T1 once is pushed back toward the range d3. An angular portion T4 below the contact portion T1 is formed in a position closer to the open end of the fixed arm 250a than the position of the contact portion T1 is (i.e., in a position far from the contact portion T2) in the longitudinal direction. When one flat portion of the cam 270 having moved from the position of the contact portion T2 comes into contact with the contact portion T1, the cam 270 is rotated until the opposite flat portion comes into contact with the contact portion T2. Then, when the cam 270 is pushed back again from the contact portion T1 toward the range d3, the opposite flat portion comes into contact with the contact portion T2 to rotate the cam 270 to an orientation allowed to go back into the passage 220. The shape of the passage 220 of the fixed arm 250a in the range d4 is designed to lock and unlock sliding of the movable arm 250b of the stay 250 in the range d2 in which the ratchet 110 does not lock.

An operation of the ophthalmic apparatus configured as above will be explained with a focus on an operation of the rotation restricting member 100 based on settings of the tilt angle of the monitor 7. Firstly, an examiner instructs an examinee to sit in a chair and fixes the examinee's face (head) with the head supporting unit 2. The examiner then takes a seat opposite the examinee and performs alignment of the examination unit 3 with respect to the eye E by operation of the joystick 5 while observing an anterior segment image (a photographed image) displayed on the monitor 7. If the examinee's eyelid is down at that time, measurement errors are liable to occur due to insufficient alignment or automatic tracking conditions. To avoid such defects, therefore, the examiner conducts an examination while lifting up the examinee's eyelid. At that time, the examiner is in a standing position and helps the examinee's eye E open by extending examiner's arm and lifting up the examinee's eyelid with fingers. In this case, the screen of the monitor 7 vertically placed is hard to view. Further, depending on the examiner's body height, the screen of the monitor 7 placed almost vertically with respect to the main unit 1 may be hard to view. In such a case, the examiner firstly rotates (tilts) the monitor 7 to change the tilt angle of the monitor 7.

The operation of the rotation restricting member 100 in association with rotation of the monitor 7 will be explained below. In the initial position of the monitor 7 shown in FIG. 2A, the ratchet 110 and the stay 250 constituting the rotation restricting member 100 are in a most contracted state as shown in FIGS. 3A and 4A. When the monitor 7 is rotated upward by the examiner, the movable arm 110b of the ratchet 110 and the movable arm 250b of the stay 250 slide in the fixed arms 110a and 250a respectively in association with rotation of the monitor 7. Thus, the rotation restricting member 100 is extended. At that time, while the monitor 7 is at a tilt angle (e.g., in a range from 0° to 85° inclusive), the pawl 161 of the ratchet 110 is positioned on the engagement portion 151 as shown in FIG. 3B. On the other hand, the cam 270 of the stay 250 is positioned in the range d3 of the passage 220. In this state, when the examiner releases his/her hand(s) from the monitor 7, the monitor 7 is rotated back (reversely rotated) by its own weight toward the initial position (an angle 0°) relative to the main unit 1 through the rotation axis L. The pawl 161 then engages with one tooth 151a, thereby stopping the reverse rotation of the monitor 7. Accordingly, the monitor 7 is fixed at a predetermined tilt angle and locked against the pressure applied from a vertical direction to the monitor 7.

When the monitor 7 is largely tilted and held in an almost horizontal position, thus further upward rotation of the monitor 7 over the first maximum tilt lock position (e.g., more than 85° but 93° or less), the pawl 161 is in the range d2 in which the protrusion 161a is pressed and fixed by the leaf spring 163, placing the ratchet 110 in an unlocked state. On the other hand, the cam 270 of the stay 250 is positioned rotatably in the range d4.

Figure 5A:
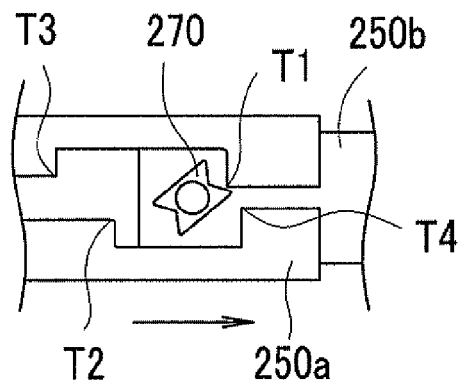
FIGS. 5A to 5E are explanatory views to show the structure of the stay of the rotation restricting member.

The operation of the monitor 7 in this state will be explained below with reference to enlarged views of the stay 250 in FIGS. 5A to 5E. As shown in FIG. 5A, firstly, upward rotation of the monitor 7 brings one of the constricted portions 270a of the cam 270 positioned in the range d4 into contact with the contact portion T1. The rotation of the monitor 7 is thus restricted. This is the maximum tilt angle θ2 of the monitor 7 (at that time, the rotation restricting member 100 is in a most extended state). At that time, the cam 270 is rotated by contact with the contact portion T1 so that the other constricted portion 270a faces in a direction to come into contact with the contact portion T2.

Figure 5B:
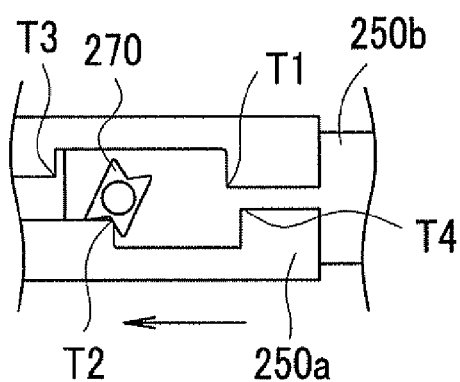

When the monitor 7 in the state shown in FIG. 5A is released from the hand(s), the monitor 7 is reversely rotated by its own weight toward the initial position. At that time, as shown in FIG. 5B, the movable arm 250b is moved in a direction indicated by an arrow until the other constricted portion 270a of the cam 270 comes into contact with the contact portion T2. When this constricted portion 270a contacts with the contact portion T2, the monitor 7 is stopped reversely rotating and thus held in a fixed, almost horizontal state, that is, the second lock position (this position of the monitor 7 is indicated by a dotted line in FIG. 2C). On the other hand, the cam 270 contacts with the contact portion T2 at that time and thus is rotated until a flat portion not shown of the cam 270 faces in a direction to come into contact with the contact portion T1. In other words, with the rotation restricting member 100 configured as above, the monitor 7 is easily locked at a desired tilt angle by simple rotation.

Returning to the explanation of operation for eye examination, the examiner adjusts the monitor 7 at the desired tilt angle by rotating the monitor 7 in the above manner, and then performs alignment between the examinee's eye E and the examination unit 3 based on the examinee's anterior segment image displayed on the monitor 7. The examiner inputs various measurement conditions on the touch panel 7a and performs a measurement on the eye refractive power of the eye E. At that time, the input operation by the examiner applies downward pressure on the monitor 7. However, the monitor 7 is prevented from oscillating by being locked by the rotation restricting member 100. This enables the examiner to correctly perform input operation on the touch panel 7a.

With the use of the rotation restricting member 100 consisting of a combination of the ratchet 110 and the stay 250 having the above configurations, it is possible to easily fix the monitor 7 by simple rotation thereof at an arbitrary tilt angle easy for the examiner to use irrespective of the position or the body height of the examiner. Locking by the rotation restricting member 100 prevents the monitor 7 from oscillating when pressure is applied thereon. This enables the examiner to more correctly input measurement conditions and others.

Figure 5C:
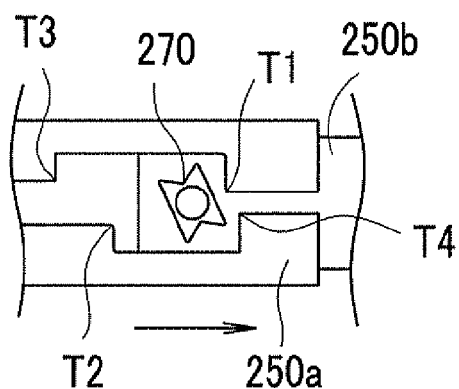
Figure 5D:
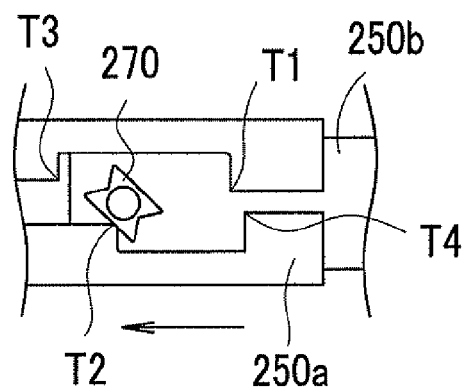
Figure 5E:
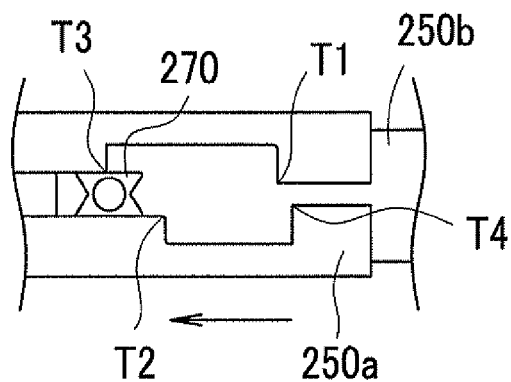

When the tilt angle of the monitor 7 set once is to be changed, unlocking of the monitor 7 is performed. For this end, the monitor 7 is rotated again up to the maximum tilt angle θ2. In the rotation restricting member 100, accordingly, the flat portion of the cam 270 contacts with the contact portion T1 as shown in FIG. 5C. At that time, the angular portion T4 below the contact portion T1 is located more to the right than T1 is, so that the cam 270 is rotated until the opposite flat portion thereof faces in a direction to come into contact with the contact portion T2. When released from the above state, the monitor 7 is reversely rotated by its own weight toward the initial position. At that time, as shown in FIG. 5D, the other flat portion of the cam 270 contacts with the contact portion T2, so that the cam 270 is rotated to an orientation allowed to go through the passage 220 as shown in FIG. 5E. From this state, the monitor 7 is pushed back by its weight or by the examiner to return to the initial position. As above, unlocking of the monitor 7 can be easily performed by simply rotating the monitor 7 again to the maximum tilt angle.

Figure 6A:
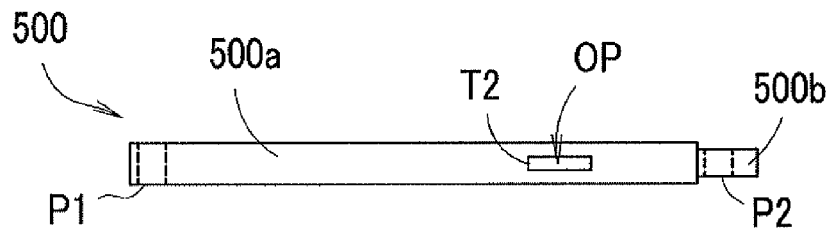
FIGS. 6A to 6E are explanatory views to show a structure of a rotation restricting member in a second embodiment.
Figure 6B:
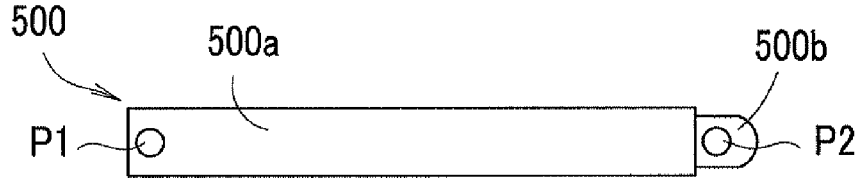
Figure 6C:
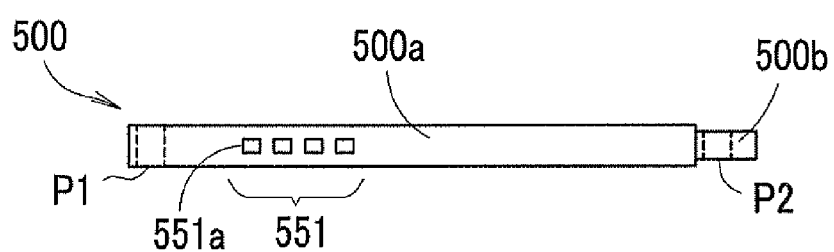
Figure 6D:
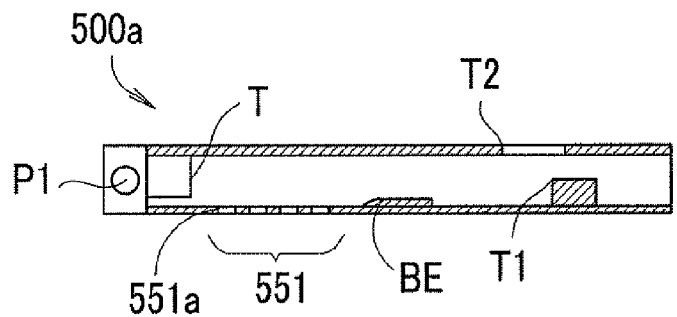
Figure 6E:
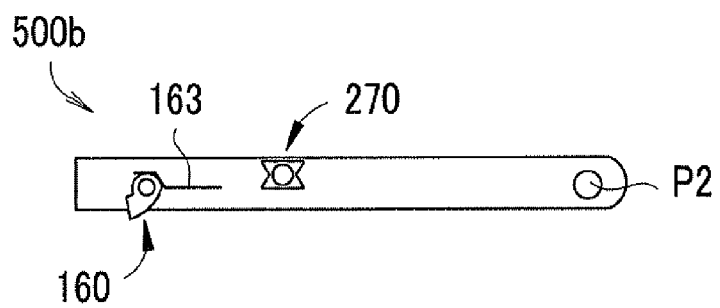

The method of locking the monitor 7 at a predetermined tilt angle is not limited to the above one. For instance, a rotation restricting member that integrally includes the functions of the ratchet 110 and the stay 250 may be adopted. FIG. 6A to 6E are explanatory views showing a structure of a rotation restricting member 500 in a second embodiment. Specifically, FIG. 6A to 6C are a top view, a front view, and a bottom view showing an external structure of the rotation restricting member 500, FIG. 6D is an explanatory view showing an internal structure of a fixed arm 500a, and FIG. 6E is an explanatory view showing a movable arm 500b. Further, FIGS. 7A to 7D are explanatory views showing motions of the rotation restricting member 500. In FIGS. 6A to 6E and FIGS. 7A to 7D, identical parts or parts having the same functions as those in the rotation restricting member 100 are explained with the same reference signs as those in the rotation restricting member 100.

In FIGS. 6A to 6C, the rotation restricting member 500 consists of the fixed arm 500a and the movable arm 500b. The fixed arm 500a is configured as a hollow casing. The movable arm 500b is formed in a thick flat plate-like shape having a size fittable in a hollow through hole (an insertion hole) of the fixed arm 500a. One end of the fixed arm 500a is fixed to a main unit 1 with a fastening fitting P1 and one end of the movable arm 500b is fixed to a monitor 7 with a fastening fitting P2. On the other hand, the other ends of the fixed arm 500a and the movable arm 500b are open ends, so that the movable arm 500b slides inside the fixed arm 500a in association with rotation of the monitor 7, thereby extending and contracting the rotation restricting member 500 in its longitudinal direction.

In FIGS. 6A to 6D, the fixed arm 500a is formed, on one side surface of the casing (on an outer side), with an engagement portion 551 including a plurality of openings. Teeth 551a formed by the openings of the engagement portion 551 correspond to predetermined tilt angles at each of which the monitor 7 is locked. Accordingly, the teeth 551a contact with a pawl locking mechanism 160 (mentioned later) to lock the monitor 7 at a desired tilt angle (including the first maximum tilt position) (the number of teeth is simplified for sake of convenience in the figure). An opposite side surface to the engagement portion 551 is formed with an opening OP. This opening OP is formed in a position corresponding to a position where the monitor 7 is locked and unlocked at a maximum tilt lock position. When a cam 270 mentioned later comes into contact with a contact portion T2 formed by the opening OP, the monitor 7 is locked at the maximum tilt lock position, (thus, the second tilt lock position). In a case where the fixed arm 500a has a sufficient space for rotation of the cam 270, the opening OP may be omitted. In this case, a contact portion T2 with which the cam 270 comes into contact is formed in an internal space of the fixed arm 500a.

Inside the casing of the fixed arm 500a, there are formed a contact portion T for returning the rotation restricting member 500 to a lock enabling state, a contact portion T1 for determining a rotation angle of the monitor 7 by the cam 270 mentioned later, and a sloped surface BE for positioning a leading end 161p of the pawl locking mechanism 160 at a rotation angle off the teeth 551a. The contact portion T is formed in a position where the contact portion T comes into contact with the pawl locking mechanism 160 when the monitor 7 is in an almost vertical position. The contact portion T1 is formed in such a position that the contact portion T1 comes into contact with the cam 270 when the monitor 7 is rotated to a maximum tilt angle θ2. The sloped surface BE is formed in correspondence with the position of the pawl locking mechanism 160 while the cam 270 is in contact with the contact portion T1.

On the other hand, the movable arm 500b shown in FIG. 6E is attached with both the pawl locking mechanism 160 and the cam 270. While the movable arm 500b is moving through a passage 520 of the fixed arm 500a, the pawl locking mechanism 160 is pushed out of the openings of the engagement portion 551 by the elastic force of the leaf spring 163. The pawl locking mechanism 160 is attached in such a position as to touch the sloped surface BE while moving across the sloped surface BE. In contrast, the cam 270 is attached in such a position as not to touch the sloped surface BE while passing by the sloped surface BE. The cam 270 is also attached in such a position as to come into contact with the contact portions T1 and T2 in the range of the opening OP and thereby rotate. Further, the pawl locking mechanism 160 and the cam 270 of the movable arm 500b are located in a positional relationship that the cam 270 comes into contact with the contact portion T1 at almost the same time when the pawl locking mechanism 160 touches the sloped surface BE.

With a pair of the fixed arm 500a and the movable arm 500b configured as above, the monitor 7 is held at each tilt angle, including the first maximum tilt angle (corresponding to the function of the ratchet 110 in the first embodiment) and also locked and unlocked at the maximum tilt lock position, thus, the second tilt lock position (corresponding to the function of the stay 250 in the first embodiment).

Figure 7A:
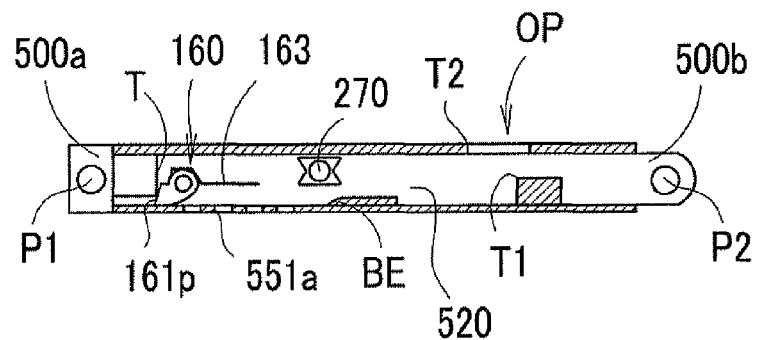
FIGS. 7A to 7D are explanatory views to show motions of the rotation restricting member in the second embodiment.
Figure 7B:
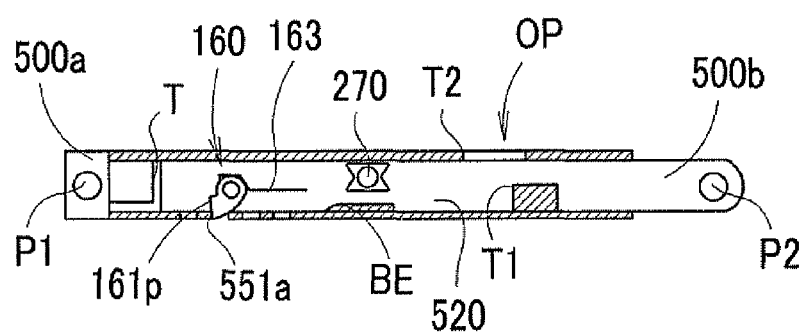
Figure 7C:
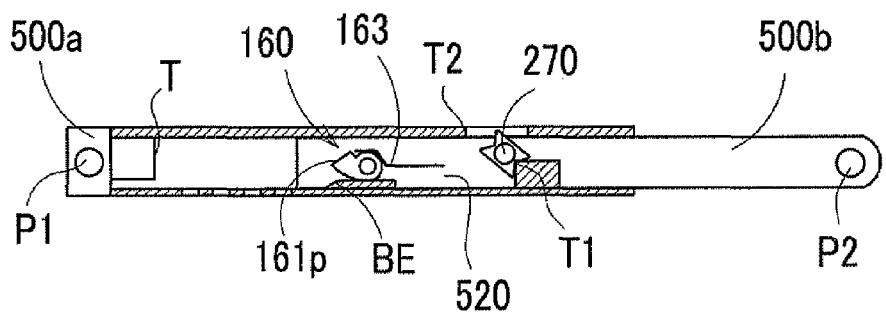
Figure 7D:
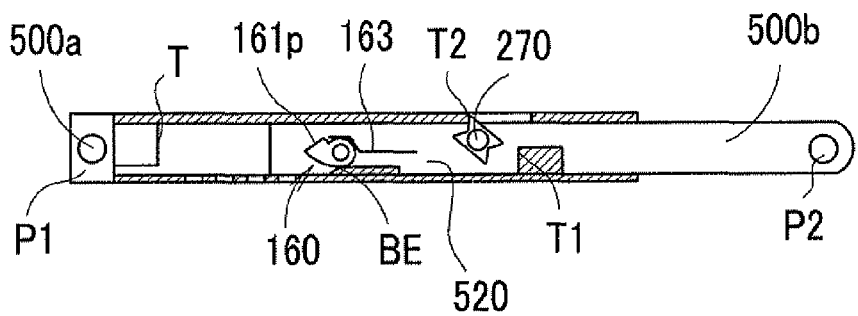

An operation to set the tilt angle of the monitor 7 using the rotation restricting member 500 having the above configuration will be explained below. FIG. 7A shows the rotation restricting member 500 in a state when the monitor 7 is in an almost vertical position (an initial position). When the monitor 7 is rotated upward from this position, the movable arm 500b is slid through the fixed arm 500a in sync with rotation of the monitor 7. At that time, when the monitor 7 is released from a held state while the pawl locking mechanism 160 is positioned in the engagement portion 551, the pawl 161 (the leading end 161p) pressed by the leaf spring 163 is engaged with one tooth 551a as shown in FIG. 7B. The monitor 7 is thus held at a predetermined tilt angle. When the monitor 7 is further rotated upward and the pawl locking mechanism 160 passes across the sloped surface BE as shown in FIG. 7C, a constricted portion 270a of the cam 270 comes into contact with the contact portion T1 at almost the same timing. Accordingly, the monitor 7 is restricted from rotating and held at the maximum tilt angle θ2. When the monitor 7 is released from the held state, the other constricted portion 270a of the cam 270 comes into contact with the contact portion T2 as shown in FIG. 7D. The monitor 7 is therefore stopped in an almost horizontal position. When the monitor 7 is rotated upward again to the maximum tilt angle, the cam 270 contacts with the contact portion T1 and thereby is rotated to change an orientation allowed to go through the passage 520 of the fixed arm 500a. In this state, when the monitor 7 is pushed back by the examiner or the gravity, the monitor 7 is returned to the initial position. The leading end 161p comes into contact with the contact portion T, thereby returning the leading end 161p to an orientation enabling a lock operation of the rotation restricting member 500.

As above, with the rotation restricting member 500 having a simpler configuration, it is possible to stop the monitor 7 at each predetermined tilt angle and also lock and unlock the monitor 7 at the maximum tilt angle.

Figure 8A:
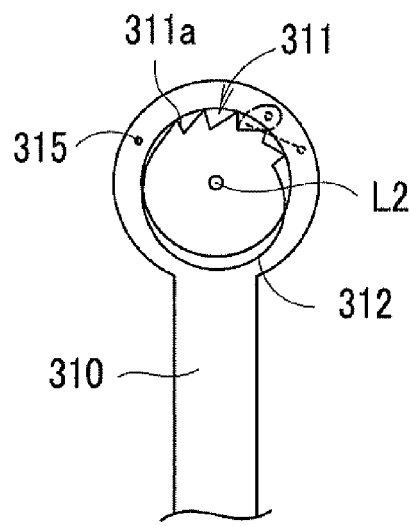
FIGS. 8A to 8D are explanatory views to show a structure and motions of a rotation restricting member in a third embodiment.
Figure 8B:
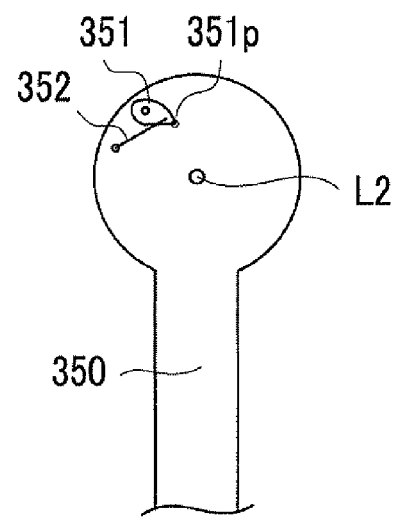
Figure 8C:
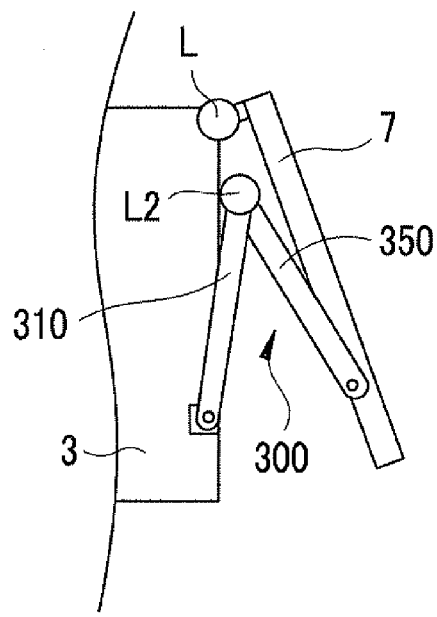

As the structure of the rotation restricting member, a rotation restricting member 300 of a rotation type shown in FIGS. 8A to 8D may also be adopted. The rotation restricting member 300 in a third embodiment consists of a combination of a first arm 310 having a circular disk shape as shown in FIG. 8A and a second arm 350 having a circular disk shape as shown in FIG. 8B. The first arm 310 integrally includes, in a circular disk part, an engagement portion 311 having a plurality of teeth 311a, a sloped surface 312 for returning the rotation restricting member 300 to an initial state, and a pin 315 for returning the rotation restricting member 300 to a lock enabling state. On the other hand, the second arm 350 is formed, in a circular disk part, with a pawl locking mechanism 351 engageable with the teeth 311a of the engagement portion 311 to lock a monitor 7. It is to be noted that a spring 352 which is an elastic member is attached to the pawl locking mechanism 351. When a leading end 351p of the pawl locking mechanism 351 is pushed up by the sloped surface 312 of the first arm 310, the leading end 351p is pulled by the spring 352 and therefore fixed in an orientation that does not engage with the engagement portion 311.

The first arm 310 and the second arm 350 mentioned above are connected to each other at respective one ends placed face to face so that the engagement portion 311 engages with the pawl locking mechanism 351 and respective rotation axes L2 coincide with each other. The other end of the first arm 310 is connected to a main unit 1 and the other end of the second arm 350 is connected to the monitor 7.

Figure 8D:
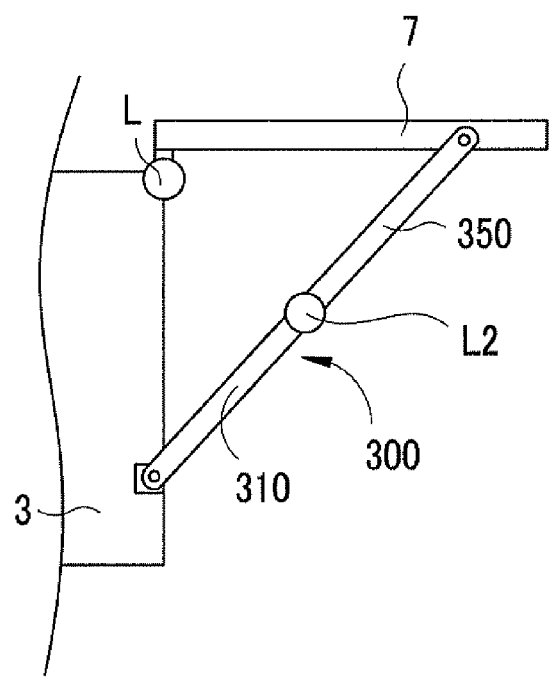

An operation of an ophthalmic apparatus provided with the rotation restricting member 300 will be explained below. When the monitor 7 is rotated from the initial position shown in FIG. 8C, the first arm 310 and the second arm 350 are rotated in opposite directions about the rotation axis L2 as shown in FIG. 8D. When the monitor 7 is then released from a held state while the leading end 351p is engaged with the teeth 311a, the monitor 7 is fixed at a predetermined tilt angle. When the monitor 7 is further rotated, causing the pawl locking mechanism 351 to be pushed up by the sloped surface 312, and then monitor 7 is released from the held state, the monitor 7 is reversely rotated by its weight to return toward the initial position. The pawl locking mechanism 351 hits against the pin 315, returning the orientation of the leading end 351p. Thereby, the rotation restricting member 300 comes back to a lock enabling state.

Figure 9A:
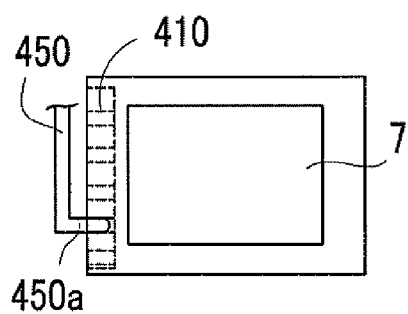
FIGS. 9A to 9B are explanatory views to show a structure and motions of a rotation restricting member in a fourth embodiment
Figure 9B:
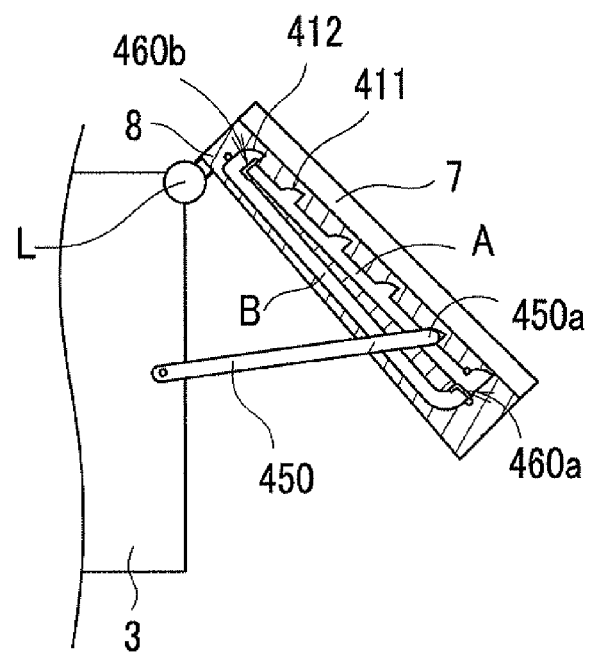

Furthermore, in a fourth embodiment shown in FIGS. 9A and 9B, an opening 410 is formed in a side surface of a holding member 8 that is rotated together with the monitor 7. An L-shaped rod-like slide part 450 is attached to a side surface of an examination unit 3 through a spring not shown. A leading end 450a of the slide part 450 is made of an elastic member. With the above configuration, the slide part 450 is slid within the opening 410 to lock and unlock the monitor 7.

FIG. 9A is a front view of the monitor 7 and FIG. 9B is an explanatory view showing a positional relationship between the opening 410 and the slide part 450 when viewed from side. The opening 410 includes a passage A and a passage B formed extending annularly in the side surface of the holding member 8. The passages A and B formed in the monitor 7 side are designed to have a width allowing the leading end 450a of the slide part 450 to move therealong. The passage A is formed with a plurality of recesses (an engagement portion) 411 at predetermined intervals. Each recess 411 has a size enough to engage with the leading end 450a of the slide part 450. Each recess (the engagement portion) 411 is formed to have a gently slope in a forward movement direction of the leading end 450a and a steep slope in an opposite direction thereto. This configuration allows the monitor 7 to rotate in one direction and the leading end 450a to press against the engagement portion 411 by its elastic force to lock the monitor 7. An engagement portion 412 formed at an end of the passage A (in a closest position to a rotation axis L) serves to lock the monitor 7 in a maximum tilt lock position when the monitor 7 is rotated to a maximum tilt angle θ2. In changeover positions on both sides of each passage A and B, L-shaped rotation members 460a and 460b are attached to be rotatable at predetermined rotation angles through springs not shown. Accordingly, one of the passages A and B is blocked to select a passage allowing the leading end 450a to pass therethrough.

An operation of an ophthalmic apparatus configured as above will be explained below. When the monitor 7 is rotated upward, the leading end 450a is moved along the passage A in a direction approaching to the rotation axis L (i.e., in the forward movement direction). At that time, when the monitor 7 is stopped rotating while the leading end 450a is being engaged in the engagement portion 411, the leading end 450a is stopped by the engagement portion 411. Thus, the monitor 7 is locked at a predetermined tilt angle.

When the monitor 7 is further rotated, the leading end 450a is positioned in the engagement portion 412 and the monitor 7 is locked at a maximum tilt angle. When the monitor 7 is further rotated from this position, the leading end 450a is moved into the passage B by rotating the rotation member 460b. Thereby, the monitor 7 is released from a locked state at the maximum tilt angle. Then, when an examiner pushes the monitor 7 back, the leading end 450b is moved into the passage A again by rotating the rotation member 460a, so that the slide part 450 is enabled again to lock the monitor 7.

While the presently preferred embodiment of the present invention has been shown and described, it is to be understood that this disclosure is for the purpose of illustration and that various changes and modifications may be made without departing from the scope of the invention as set forth in the appended claims.

The invention claimed is:
1. An ophthalmic apparatus comprising:
   a main unit including a photographing device for photographing an examinee's eye;
   a monitor provided in the main unit, the monitor including a displaying device for displaying an image of the eye photographed by the photographing device and a setting device for setting a predetermined function;

a rotation mechanism for rotating the monitor from an almost vertical position to an almost horizontal position with respect to the main unit;

a first lock mechanism for locking the monitor at each predetermined tilt angle, the first lock mechanism being arranged to allow upward rotation of the monitor but restrict downward rotation of the monitor in the course of rotating the monitor from the almost vertical position to the almost horizontal position; and a first unlock mechanism arranged to release the restriction of the downward rotation of the monitor by the first lock mechanism based on further upward rotation of the monitor after the monitor is locked in a first maximum tilt lock position by the first lock mechanism.

2. The ophthalmic apparatus according to claim 1, further comprising:

a second lock mechanism for locking the monitor to allow the upward rotation of the monitor but restrict the downward rotation of the monitor in a second tilt lock position having a tilt angle larger than that of the first maximum tilt lock position by the first lock mechanism, the second tilt lock position being a position at which the first unlock mechanism releases the restriction of the downward rotation of the monitor by the first lock mechanism; and a second unlock mechanism arranged to release the restriction of the downward rotation of the monitor by the second lock mechanism when the monitor locked in the second tile lock position by the second lock mechanism is further rotated upward.

3. The ophthalmic apparatus according to claim 2, wherein the first lock mechanism and the first unlock mechanism is a ratchet mechanism, and the second lock mechanism and the second unlock mechanism is a flap stay.

4. The ophthalmic apparatus according to claim 2, wherein the second tilt lock position by the second lock mechanism is the almost horizontal position, and the first maximum tilt lock position by the first lock mechanism has a tilt angle smaller than that of the second tilt lock position.

5. The ophthalmic apparatus according to claim 1, wherein the first lock mechanism includes a fixed arm and a movable arm slidably fitted in the fixed arm, the fixed arm is formed with an engagement portion formed of a plurality of teeth or a plurality of openings in a passage of the fixed arm in which the movable arm slides, and the movable arm is formed with a pawl locking member engageable with the teeth or the openings.

6. The ophthalmic apparatus according to claim 1, wherein the setting device provided in the monitor is a touch panel.

* * * * *